US009968135B2

(12) United States Patent
Liu

(10) Patent No.: US 9,968,135 B2
(45) Date of Patent: May 15, 2018

(54) ELECTRONIC CIGARETTE WITH OIL OBSERVATION STRIP

(71) Applicant: KIMREE HI-TECH INC., Road Town, Tortola (VG)

(72) Inventor: Qiuming Liu, Shenzhen (CN)

(73) Assignee: HUIZHOU KIMREE TECHNOLOGY CO., LTD., Shenzhen Branch (CN)

( * ) Notice: Subject to any disclaimer, the term of this patent is extended or adjusted under 35 U.S.C. 154(b) by 0 days. days.

(21) Appl. No.: 15/118,756

(22) PCT Filed: Feb. 12, 2014

(86) PCT No.: PCT/CN2014/072005
§ 371 (c)(1),
(2) Date: Aug. 12, 2016

(87) PCT Pub. No.: WO2015/120589
PCT Pub. Date: Aug. 20, 2015

(65) Prior Publication Data
US 2017/0042229 A1    Feb. 16, 2017

(51) Int. Cl.
*A24F 47/00*    (2006.01)
*B65D 25/56*    (2006.01)
*A61M 15/06*   (2006.01)

(52) U.S. Cl.
CPC ............ *A24F 47/008* (2013.01); *B65D 25/56* (2013.01); *A61M 15/06* (2013.01)

(58) Field of Classification Search
CPC ................................ A24F 47/00; A61M 15/06
(Continued)

(56) References Cited

U.S. PATENT DOCUMENTS 7,997,280 B2 * 8/2011 Rosenthal ............ A61M 11/041
128/202.21
8,528,569 B1 * 9/2013 Newton ................. A24F 47/008
128/202.21
(Continued)

FOREIGN PATENT DOCUMENTS

CN    202714190 U    2/2013
CN    203121010 U    8/2013
(Continued)

OTHER PUBLICATIONS

International Search Report (ISR) issued by the State Intellectual Property Office of the Peoples Republic of China dated Jul. 30, 2014 for PCT/CN2014/072005, China.

*Primary Examiner* — Vanessa Girardi
(74) *Attorney, Agent, or Firm* — Tim Tingkang Xia, Esq.; Locke Lord LLP

(57) ABSTRACT

An electronic cigarette comprises an electronic cigarette body; the electronic cigarette body is provided with a smoking end (1), an oil storage assembly (4) for containing cigarette oil, an atomization assembly (3) for atomizing the cigarette oil and a battery component (2) for powering the atomization assembly (3); the oil storage assembly (4) is arranged on one end of the electronic cigarette body which is in an opposite side of the smoking end (1), since a smoke passage does not pass through the oil storage assembly (4), a user can be effectively prevented from sucking a non-atomized cigarette oil; and meanwhile, through an arrangement of a protective sleeve (5) for containing the oil storage assembly (4) on the electronic cigarette, a vibration-resistance of the oil storage assembly (4) can be enhanced, so that a risk that the oil storage bottle is easily broken is avoided.

14 Claims, 6 Drawing Sheets

(58) Field of Classification Search
USPC ............ 131/329, 270, 273, 347; 128/202.21, 128/203.23, 203.27
See application file for complete search history.

(56) References Cited

U.S. PATENT DOCUMENTS

| | | | | |
|---|---|---|---|---|
| 2015/0107609 A1* | 4/2015 | Liu | ........................ | A24F 47/008 131/329 |
| 2015/0164141 A1* | 6/2015 | Newton | .............. | H01M 2/1055 131/329 |
| 2016/0270442 A1* | 9/2016 | Liu | ........................ | A24F 47/008 |
| 2017/0049152 A1* | 2/2017 | Liu | ........................ | A24F 47/008 |
| 2017/0172207 A1* | 6/2017 | Liu | ........................ | A24F 47/008 |

FOREIGN PATENT DOCUMENTS

| | | | |
|---|---|---|---|
| CN | 103355745 A | | 10/2013 |
| CN | 203314099 U | | 12/2013 |
| GB | 2504076 A | | 1/2014 |
| KR | 20140013653 A | | 2/2014 |

* cited by examiner

ELECTRONIC CIGARETTE WITH OIL OBSERVATION STRIP

TECHNICAL FIELD

The present application relates to the technical field of an electronic products, and more particularly, relates to an electronic cigarette.

BACKGROUND

As shown in FIG. 1, an electronic cigarette in the prior art comprises a battery component 2', an atomization assembly 3', an oil storage assembly 4', in the prior art, the battery component 2' is connected with the atomization assembly 3' by threading, the oil storage assembly 4' is connected with the atomization assembly 3' by threading as well, an air inlet 1' is defined on the oil storage assembly 4' and is communicated with a smoke passage to discharge smoke. When using, a battery of the battery component 2' supplies an electrical power to a heating coil inside the atomization assembly 3', so that the heating coil can generate heat to heat and atomize cigarette oil in the oil storage assembly 4', thus the smoke which is inhaled by users can be produced.

In the prior art, the oil storage assembly mainly includes two types, one of them is an oil storage cotton while the other is an oil storage bottle. The oil storage cotton is made of a loose and porous materials such as foam, and the oil storage cotton stores the cigarette oil by a means of adsorption. As the oil storage cotton is soft, it is convenient to be installed and sealed inside the atomization assembly 3', and will not be damaged by a collision and a vibration from an external environment. However, an amount of the cigarette oil which is stored by the oil storage cotton is generally small, and it is difficult to maintain a need for using the electronic cigarette in a continuous long time. Further, as the oil storage cotton is needed to be sealed inside the atomization assembly 3' to prevent a volatilization of the cigarette oil, after exhausting the cigarette oil which is absorbed by the oil storage cotton, an outer casing of the atomization assembly 3' should be opened to add cigarette oil to the oil storage cotton or change the oil storage cotton, this operation is complicated, thus, the oil storage bottle is generally applied for the oil storage assembly, nevertheless, in the prior art, the oil storage bottle contains following defects:

1). The oil storage bottle is generally made of glass, and detachably installed outside the atomization assembly 3' by plugging, screwing etc. Compared with the oil storage cotton, a capacity of the oil storage bottle is greater, and only need to remove the oil storage bottle when filling the cigarette oil or changing the oil storage bottle, it is no need to open the outer casing of the atomization assembly 3', thus the operation is simple. However, the oil storage bottle is easy to be broken when suffering a collision and a vibration from an external environment.

2). As in the prior art, the oil storage bottle is installed at an end close to mouth, and the oil storage bottle is defined in the smoke passage, thus, the cigarette oil in the oil storage bottle is easy to leak to the smoke passage, resulting a problem that the cigarette oil is inhaled by users before atomizing; during smoking, a mouth holds on the oil storage bottle, different volumes of the cigarette oil are outputted to the atomization assembly 3' as the oil storage bottle is held by different holding force, leading to an unstable amount of smoke, and it is easy to cause a leakage of the cigarette oil; besides, as the battery component 2' and the atomization assembly 3' are heavy, under an action of gravity of both the battery component 2' and the atomization assembly 3', gaps due to bending deformation are easy to happen at a connection point of the oil storage bottle and the atomization assembly 3', thus, it is easy to cause leaked cigarette oil, and users are easy to inhale the leaked cigarette oil.

Therefore, defects are existed in the prior art, and needed to be improved.

BRIEF SUMMARY

The object of the present application is to provide an electronic cigarette which enables a pure taste, exempts from a leakage of the cigarette oil and comprises an oil storage assembly which has a vibration resistance, aiming at the drawbacks in the prior art that the oil storage bottle is easy to be broken, and easy to leak the cigarette oil, the users are easy to inhale a cigarette oil condensation and the cigarette oil condensation is easy to block the smoke passage.

A technical proposal adopted by the present invention to solve technical problems is to provide an electronic cigarette, comprises an electronic cigarette body, wherein, the electronic cigarette body is provided with a smoking end, an oil storage assembly for containing cigarette oil, an atomization assembly for atomizing the cigarette oil and a battery component for powering the atomization assembly; the oil storage assembly is arranged on one end of the electronic cigarette body which is on an opposite side of the smoking end, the electronic cigarette further comprises a protective sleeve for containing the oil storage assembly.

Advantageously, an observation zone which is used for observing an amount of the cigarette oil in the oil storage assembly is defined on the protective sleeve.

Advantageously, the observation zone is a strip through hole or a strip transparent piece which is defined along an axial direction of the electronic cigarette.

Advantageously, a bottom of the protective sleeve which is on the opposite side of the smoking end is a cambered surface, or an arc protrusion is formed along an axial direction of the protective sleeve and extends toward an opposite side of the smoking end, the cambered surface or the arc protrusion is provided with a pattern.

Advantageously, the oil storage assembly is a transparent glass product or a ceramic product, and the protective sleeve is a metal product, a wood product or a foam product.

Advantageously, the atomization assembly is located between the battery component and the oil storage assembly, and the smoking end is defined outside an end of the battery component, or the smoking end is placed in a middle part of the battery component, or the smoking end is arranged at a position of the battery component which is an opposite side of the atomization assembly.

Advantageously, the protective sleeve is detachably connected with the atomization assembly.

Advantageously, the protective sleeve is connected with the atomization assembly by a thread connection, the protective sleeve has a first internal thread, the atomization assembly comprises a first connecting piece, the first connecting piece has a first external thread which is matched with the first internal thread.

Advantageously, the protective sleeve is interference fitted with the atomization assembly, a compression ring is arranged at a connection point of the atomization assembly and the oil storage assembly, the protective sleeve is sheathed on the compressing ring.

Advantageously, the oil storage assembly is detachably connected with the atomization assembly;

and/or the atomization assembly is detachably connected with the battery component.

Advantageously, the atomization assembly is coaxially defined with the battery component.

Advantageously, the atomization assembly comprises:

A heating coil assembly which is used for atomizing the cigarette oil;

An oil guide device which is used to transfer the cigarette oil to the heating coil assembly.

Advantageously, the atomization assembly further comprises a first connecting piece which is detachably connected with the battery component and the oil storage assembly, the first connecting piece has an atomizing chamber, the heating coil assembly and the oil guide device are installed inside the atomizing chamber, the oil guide device comprises an oil guide cotton and an atomization sleeve which is sheathed on the oil guide cotton, one end of the oil guide cotton and the atomization sleeve extend inside the oil storage assembly, at least one oil transferring hole is defined on an area of a peripheral wall of the atomization sleeve which is arranged inside the oil storage assembly, the cigarette oil is transferred to the oil guide cotton by the oil transferring hole and then the cigarette oil is transferred to the heating coil assembly to be atomized.

Advantageously, the battery component comprises a battery sleeve, a battery which is defined along the axis of the battery sleeve and an airflow control module, the smoking end is a suction nozzle which is connected with an end of the battery sleeve which is on an opposite side of the oil storage assembly, the suction nozzle is provided with an air inlet which is communicated with an inside part of the battery sleeve.

Advantageously, the battery component further comprises a vent tube which is defined along an axial direction of the battery component, the vent tube is used to communicated the air inlet with a part of a smoke passage of the atomization assembly.

Advantageously, the atomization assembly is connected with the oil storage assembly by a thread connection, the atomization assembly is connected with the battery component by an inserting connection.

Advantageously, a first sealing ring, which is used for sealing the oil storage assembly, is defined at a detachable connection point of the atomization assembly and the oil storage assembly;

Advantageously, the present invention also provides a method for assembling a battery component, the method for assembling a battery component comprises following steps:

or, a ring sealing plug configuring with a through hole is defined at a mouth of the oil storage assembly (4) to seal the oil storage assembly (4), a film which is used to seal the oil storage assembly (4) is defined inside the through hole of the ring sealing plug, and the film can be pierced.

With application of the electronic cigarette, the following advantages can be achieved: by defining the oil storage assembly on one end of the electronic cigarette body, and the end being an opposite side of the smoking end, it is possible to effectively prevent users from sucking a non-atomized cigarette oil since the smoke passage does not pass through the oil storage assembly; and meanwhile, through the arrangement of a protective sleeve for containing the oil storage assembly on the electronic cigarette, the vibration-resistance of the oil storage assembly can be enhanced, so that the risk that the oil storage bottle is easily broken is avoided.

BRIEF DESCRIPTION OF THE DRAWINGS

The present application will be further described with reference to the accompanying drawings and embodiments in the following.

DETAILED DESCRIPTION OF THE PREFERRED EMBODIMENTS

The object of the present application is to provide an electronic cigarette which enables a pure taste, exempts from a leakage of the cigarette oil and comprises an oil storage assembly which has a vibration resistance, aiming at the drawbacks in the prior art that the oil storage bottle is easy to be broken, and easy to leak the cigarette oil, the users are easy to inhale a cigarette oil condensation and the cigarette oil condensation is easy to block the smoke passage.

In the present invention, by defining the oil storage assembly on one end of the electronic cigarette body, and the end being an opposite side of the smoking end, it is possible to effectively prevent users from sucking a non-atomized cigarette oil since the smoke passage does not pass through the oil storage assembly; and meanwhile, through the arrangement of a protective sleeve for containing the oil storage assembly on the electronic cigarette, the vibration-resistance of the oil storage assembly can be enhanced, so that the risk that the oil storage bottle is easily broken is avoided.

The example embodiments of the present application will be further described with referencing to the accompanying drawings, to have a clear understanding of the technical features, purposes and effects of the present invention. Obviously, the following example embodiments are only parts of the embodiments of the present application.

Figure 1:
FIG. 1 is a structure diagram of an electronic cigarette provided by the prior art.
Figure 2:
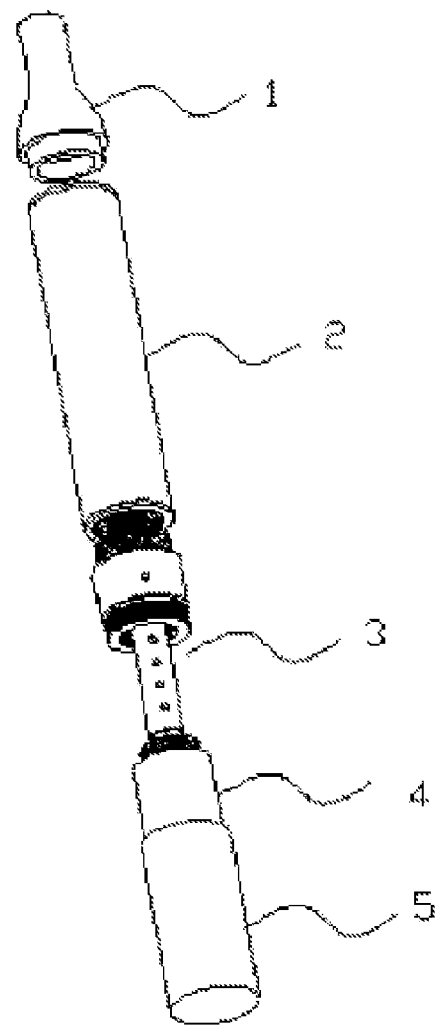
FIG. 2 is a decomposed structure of an electronic cigarette provided by a first embodiment of the present application.

Refer to FIG. 2, is a decomposed structure of an electronic cigarette provided by a first embodiment of the present application.

The electronic cigarette body is provided with a smoking end 1, an oil storage assembly 4 for containing cigarette oil, an atomization assembly 3 for atomizing the cigarette oil and a battery component 2 for powering the atomization assembly 3; users smoke by the smoking end 1, a smoke passage is formed inside the electronic cigarette body, so that users can inhale smoke which flow from the smoke passage.

The oil storage assembly 4 is arranged on one end of the electronic cigarette body which is on an opposite side of the smoking end 1, the electronic cigarette further comprises a protective sleeve 5 for containing the oil storage assembly 4.

In the present embodiment, in order to enable a general structure of the electronic cigarette to simulate a real cigarette and to in accordance with the user use habit, meanwhile, to enable an appearance of the smoke passage is simple and unobstructed, the atomization assembly 3 can be defined coaxially with the battery component 2.

The atomization assembly 3 and the battery component 2 can also be defined non coaxially, for example, the oil storage assembly 4 and the atomization assembly 3 are arranged in a parallel way, to ensure the oil storage assembly 4 and the atomization assembly 3 are connected with the battery component respectively, thus, the general structure of the electronic cigarette is shown as a "T" type, or the oil storage assembly is defined on one side of the atomization assembly to form a "L" type electronic cigarette.

Therefore, in the present embodiment, the appearance of the general structure of the electronic cigarette is not limited, as well as the oil storage assembly 4 is defined at a position which is an opposite side of the smoking end 1. Preferably, the atomization assembly 3 is defined between the battery component 2 and the oil storage assembly 4. Thus, a defect that temperature of the atomization assembly 3 is too high to hurt mouths of users which is caused by that the atomization assembly 3 is defined on a middle and upper area of the electronic cigarette which is close to the mouths can be overcome, and it has an advantage to simulate temperature of the real cigarette. As the smoke passage does not pass the oil storage assembly 4, it is possible to overcome a condensation problem which is caused by that heat of the smoke is absorbed by the cigarette oil of the oil storage assembly 4, thus to effectively prevent users from sucking a non-atomized cigarette oil, then a blocking problem of the smoke passage which is caused by the cigarette oil condensation can be avoided, and users' experience is improved.

In the present embodiment, the atomization assembly 3 is located between the battery component 2 and the oil storage assembly 4, and the smoking end 1 is defined outside an end of the battery component 2, the smoking end is a suction nozzle, so that an appearance of the electronic cigarette can simulate a real cigarette by this defining means.

Certainly, a specific way from defining the smoking end 1 in the present embodiment is not limited, the smoking end 1 can be defined outside an end of the battery component 2, or the smoking end 1 is placed in a middle part of the battery component 2, or the smoking end 1 is arranged at a position of the battery component 2 which is an opposite side of the atomization assembly 3. For instance, the battery component 2, the atomization assembly 3 and the oil storage assembly 4 can be staggered arranging, so as to enable a general appearance of the electronic cigarette is a special shape, a specific shape of the special shape can be any shape.

In the present embodiment, the atomization assembly 3 is detachably connected with the battery component 2, so as to replace the atomization assembly 3 conveniently, the oil storage assembly 4 is detachably connected with the atomization assembly 3 while the protective sleeve 5 is detachably connected with the atomization assembly 3, so that the users can fill the cigarette oil or replace the oil storage assembly 4 conveniently.

Wherein, the oil storage assembly 4 is a transparent glass product or a ceramic product, thus, quality of the cigarette oil which is stored in the oil storage assembly 4 is difficult to be changed, the protective sleeve 5 is a metal product, a wood product or a foam product, if the electronic cigarette falls down or be hit by an accident, the protective sleeve will not be broken, selections for materials can be various, designs for an appearance of an outer casing can be various as well.

An observation zone which is used for observing an amount of the cigarette oil in the oil storage assembly 4 is defined on the protective sleeve 5, users can observes a remain amount of the cigarette oil by the observation zone, so as to fill the cigarette oil easily or replace the oil storage assembly 4 in time, avoiding the heating coil in the atomization assembly 3 burning itself then results in a damage of components, even generates harmful gas which affects the health of the users after the cigarette oil was exhausted.

Figure 3:
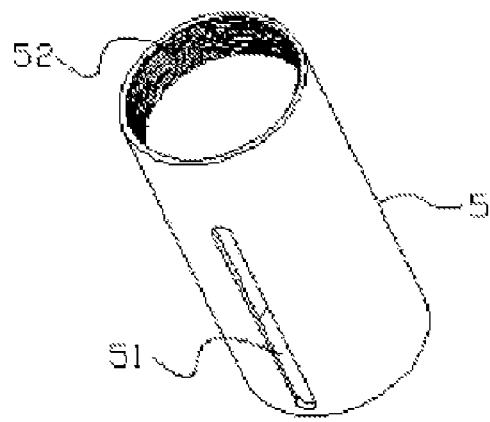
FIG. 3 is an appearance schematic diagram of a protective sleeve of an electronic cigarette provided by a first embodiment of the present application.
Figure 4:
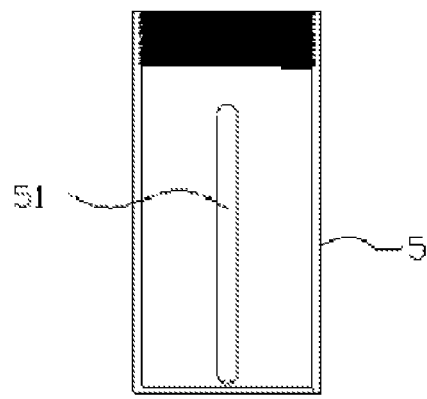
FIG. 4 is a cutaway view of a protective sleeve of an electronic cigarette provided by a first embodiment of the present application.
Figure 9:
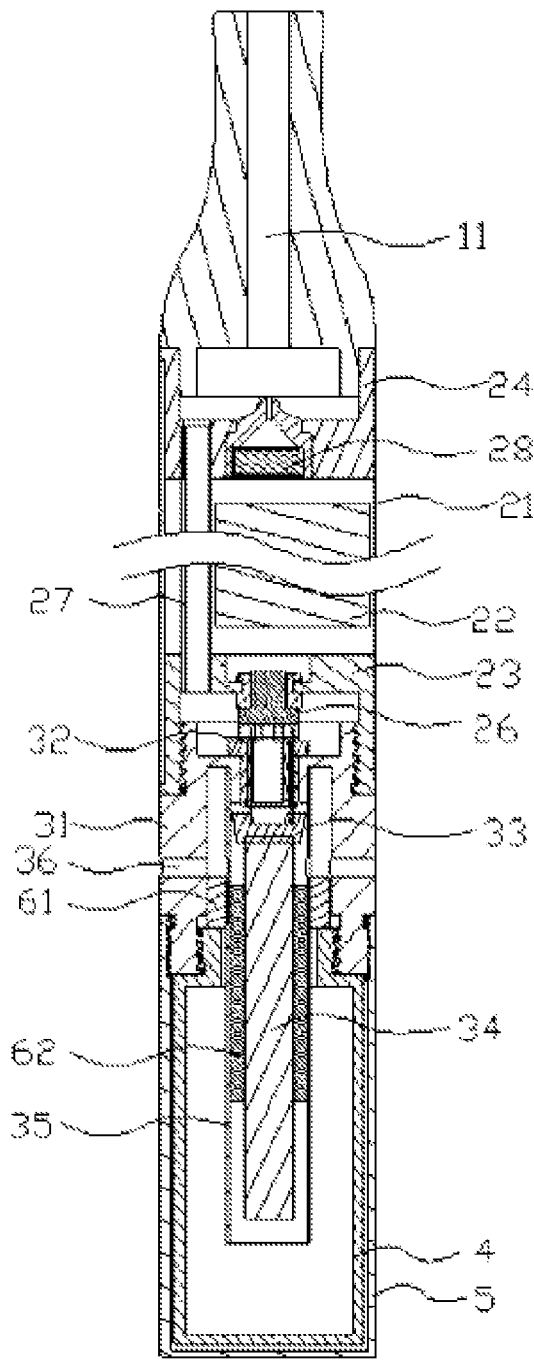
FIG. 9 is a cutaway view of the electronic cigarette shown in FIG. 2.

Specifically, referring to FIG. 3 and FIG. 4, the protective sleeve 5 is a cylinder with an opening end, an inner sidewall of the opening end of the protective sleeve 5 is provided with a first internal thread 52, an inside part of the protective sleeve 5 has a space to accommodate the oil storage assembly 4, the oil storage assembly 4 is connected to the atomization assembly 3, then the protective sleeve 5 is sheathed on the oil storage assembly 4, and threaded connected to the atomization assembly 3 through the first internal thread, details about the connection part is shown in a description to FIG. 9.

Wherein, a strip through hole 51 is defined along an axial direction of the electronic cigarette, the strip through hole 51 can be the observation zone, the observation zone can be a strip transparent piece as well. Regions outside of the strip through hole 51 or the strip transparent piece is also the observation zone and can be designed with various appearance technologies, or covered by all kinds of beautiful drawings. Preferably, a scale can be arranged in the regions along an axial direction of the observation zone, so that the users can estimate a time for smoking the amount of residual cigarette oil, and make it convenient for the users to use.

Figure 5:
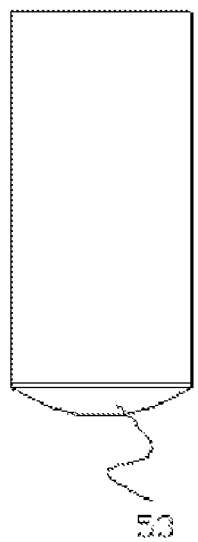
FIG. 5 is an appearance schematic diagram of a protective sleeve of an electronic cigarette provided by a second embodiment of the present application.
Figure 6:
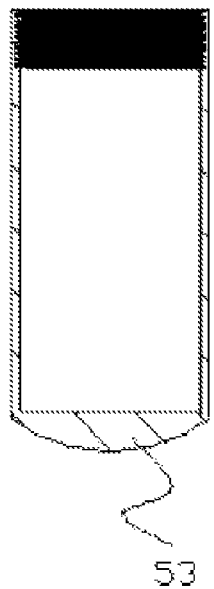
FIG. 6 is a cutaway view of a protective sleeve of an electronic cigarette provided by a second embodiment of the present application.
Figure 7:
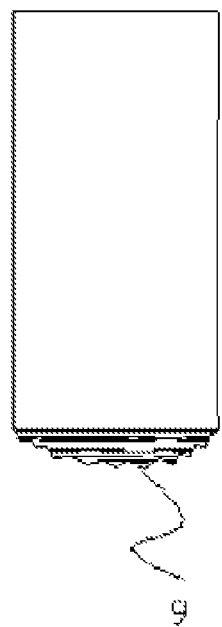
FIG. 7 is an appearance schematic diagram of a protective sleeve of an electronic cigarette provided by a third embodiment of the present application.
Figure 8:
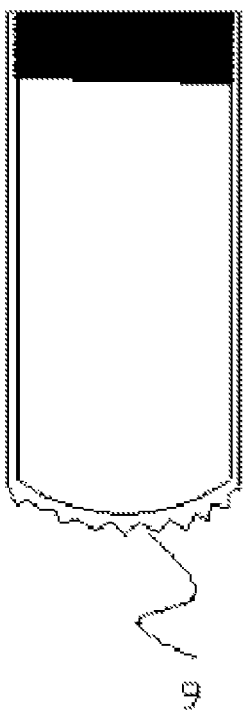
FIG. 8 is a cutaway view of a protective sleeve of an electronic cigarette provided by a third embodiment of the present application.

Referring to FIG. 5 and FIG. 6, an arc protrusion 53 is formed along an axial direction of the protective sleeve 5 and extends toward an opposite side of the smoking end 1, or referring to FIG. 7 and FIG. 8, a bottom of the protective sleeve 5 is designed as a cambered surface, the cambered surface or the arc protrusion 53 is provided with a pattern 9. In the prior art, the oil storage assembly 4 is made of glass material, so an improvement on an appearance is inconvenient, in the present invention, the oil storage assembly 4 does not need any transformation, a variety of human improvements can be produced outside the protective sleeve 5, for example, the cambered surface or the arc protrusion 53 is in order to achieve a better simulation to a real cigarette burning, and the pattern defined on the cambered surface or the arc protrusion 53 is used for a further simulation of the situation of the burning of a cigarette hand, and enhance the users' experience.

Refer to FIG. 9 which is a cutaway view of the electronic cigarette shown in FIG. 2; a general structure of the electronic cigarette in the present invention is introduced as following.

Wherein, the smoking end 1 is a suction nozzle which is connected with an end of the battery sleeve 21 which is on an opposite side of the oil storage assembly 4, the suction nozzle is provided with an air inlet 11 which is communicated with an inside part of the battery sleeve 21.

Wherein, the battery component 2 comprises a battery sleeve 21, a battery 22 which is defined along the axis of the battery sleeve 21 and an airflow control module 28, the battery component 2 further comprises a second connecting piece 23 which is used to connect the battery sleeve 21 and the atomization assembly 3, a third connecting piece 24 which is used to connect the battery sleeve 21 and the suction nozzle, and a vent tube 27 which is defined between the second connecting piece 23 and the third connecting piece 24 and along an axial direction of the battery component 2, the vent tube is used to communicated the air inlet 11 with a part of a smoke passage of the atomization assembly 3.

The second connecting piece 23 and the third connecting piece 24 are inserted to two ends of the battery sleeve 2 and tight fitted with the battery sleeve 2, the second connecting piece 23 is a hollow structure, and an inside part of the second connecting piece 23 is provided with an battery electrode 26 which is electrically connected with the battery 22, an insulating ring is defined between the second connecting piece 23 and the battery electrode 26. An installing groove is defined on an end of the third connecting piece 24 which is close to the battery 22, and the airflow control module 28 is fixed in the installing groove, through holes which are communicated with the air inlet 11 is defined at the bottom of the installing groove.

In the present embodiment, the battery sleeve 21 is detachably connected to the suction nozzle, to make it convenient for users to remove the suction nozzle to clean. Certainly, the suction nozzle and the battery sleeve 21 can be designed as an integral structure.

In the present embodiment, adding the vent tube 27 effectively reduces the smoke contacting with the battery 22 and the airflow control module 28, thus, that the cigarette oil condensation or saliva from the suction nozzle being attached to the battery 22 and the air flow control module 28 can be avoided, if the cigarette oil condensation happens, or saliva is attached to the air flow control module 28, a serious situation is that the electronic cigarette will be directly damaged and will not work again, besides, after adding the vent tube 27, the smoke flows inside the battery component 2 smoothly.

Wherein, methods for connecting the protective sleeve 5 with the atomization assembly 3 can be various, in the present embodiment, the protective sleeve 5 is connected to the atomization assembly 3 by a threaded connection, referring to FIG. 3, the opening end of the protective sleeve 5 is provided with the first internal thread 52.

The atomization assembly 3 comprises a first connecting piece 31, the first connecting piece 31 has a first external thread which is matched with the first internal thread 52. Besides, in the present embodiment, the atomization assembly 3 is connected with the oil storage assembly 4 by a thread connection, a second internal thread is defined on the first connecting piece 31 while a second external thread which is matched with the second internal thread is defined on the oil storage assembly 4.

The atomization assembly 3 comprises: a heating coil assembly 33 which is used for atomizing the cigarette oil, and an oil guide device which is used to transfer the cigarette oil to the heating coil assembly 33, in the present embodiment, the oil guide device specifically comprises an oil guide cotton 34, which is defined along an axial direction of the oil guide device, and an atomization sleeve 35 which is sheathed on the oil guide cotton 34, certainly, the oil guide device is not limited to the oil guide cotton, it can be any product that has an ability to transfer the cigarette oil, such as an oil guide string, and so on. One end of the oil guide cotton 34 faces to the heating coil assembly 33, the other end of the oil guide cotton 34 and the atomization sleeve 35 extend inside the oil storage assembly 4, at least one oil transferring hole is defined on an area of a peripheral wall of the atomization sleeve 35 which is arranged inside the oil storage assembly 4, the cigarette oil is transferred to the oil guide cotton 34 by the oil transferring hole and then the cigarette oil is transferred to the heating coil assembly 33 to be atomized.

The atomization assembly 3 further comprises a first connecting piece 31 which is threaded connected to the second connecting piece 23, and an atomization electrode 32 which is defined at the bottom sidewall of the first connecting piece 31 and connected with the battery electrode 26, the second connecting piece 23 is screwed into an inner space of the first connecting piece 31, then the atomization electrode 32 is electrically connected to the battery electrode 26. Wherein, a connecting method of the second connecting piece 23 and the first connecting piece 21 is not limited by this, it can be any detachable connection, for example, buckle connection, interference fit, etc.

The first connecting piece 31 has an atomizing chamber which is toward the oil storage assembly 4, an air through hole 36 which is communicated with the atomizing chamber is defined on a sidewall of the first connecting piece 31, the heating coil assembly 33 and the oil guide device are both defined in the atomizing chamber, an atomization electrode installing hole is defined at the bottom sidewall of the first connecting piece 31, the atomization electrode 32 is sheathed by an insulating ring and then is inserted in to the atomization electrode installing hole, wherein, a communication hole is defined on the atomization electrode 32 along an axial direction of the atomization electrode 32 and is communicated with the atomizing chamber, the heating coil assembly 33 is electrically connected to the atomization electrode 32, smoke is produced when the heating coil assemble 33 is supplied with electrical power, an airflow enters the atomizing chamber and bring a generated smoke to a gap between the atomization electrode 32 and the battery electrode 26 via the communication hole on the atomization electrode 32, then through the vent tube 27, the airflow runs into the air inlet 11 of the suction nozzle, and finally being discharged into mouths of the users. Therefore, the smoke which is atomized does not go through the oil storage assembly 4, in order to avoid the smoke is condensed inside the smoke passage, thus to effectively prevent the smoke passage from blocked by the cigarette oil condensation.

It is need to be clear that the above approach to the arrangements of the air through hole is only for example and does not be limited, as well as the air through hole in the electronic cigarette body is communicated with the smoking end 1 by the smoke passage.

Wherein, a first sealing ring 61, which is used for sealing the oil storage assembly 4, is defined at a detachable connection point of the first connecting piece 31 and the oil storage assembly 4, in details, the first sealing ring 61 is tightly sheathed on the atomization sleeve 35, the atomization sleeve 35 is inserted into an opening portion of the oil storage assembly 4 to ensure the first sealing ring 61 is abutted against an end surface of the opening portion.

Or, a ring sealing plug configuring with a through hole is defined at a mouth of the oil storage assembly 4 to seal the oil storage assembly 4, a film which is used to seal the oil storage assembly 4 is defined inside the through hole of the ring sealing plug, and the film can be pierced. When replacing the oil storage assembly 4, the atomization sleeve 35 is inserted into the oil storage assembly 4 by piercing the film. Through the pierced film, the oil storage assembly which is inserted by the automation sleeve 35 still maintains a well tightness, thus to effectively prevent a leakage of the cigarette oil.

In order to further avoid the cigarette oil in the atomization sleeve 35 leaks to the smoke passage, a second sealing ring is defined between the oil guide cotton 34 and the atomization sleeve 35.

As the suction nozzle and the oil storage assembly 4 are defined at two ends which are in an opposite sides to each other, during smoking, the problem of an unstable amount of smoke which is caused by that different volumes of the cigarette oil are outputted to the atomization assembly as the oil storage bottle is held by different holding force can be avoided, thus a stability of the amount of the smoke is improved, and it is not easy to cause a leakage of the cigarette oil; besides, gaps due to bending deformation and a problem of leakage of the cigarette oil that happens at a connection point of the oil storage bottle and the atomization assembly under an action of gravity of both the battery component 2 and the atomization assembly can be avoided, thus, the defect that users are easy to inhale the leaked cigarette oil is overcome.

Although the atomization assembly 3 and the battery component 2 and the oil storage assembly 4 are threaded connection, the atomization assembly 3 can be threaded connected to the oil storage assembly 4 while a connection between the atomization assembly 3 and the battery component 2 is inserting connection. Thus, the connection between the atomization assembly 3 and the battery component 2 will not be affected when remove the connection between the atomization assembly 3 and the oil storage assembly 4, or the connection between the atomization assembly 3 and the oil storage assembly 4 will not be affected when remove the connection between the atomization assembly 3 and the battery component 2, so as to avoid the oil storage assembly 4 is drove to be loose when users are removing the battery component 2, as the threads defined on two ends of the atomization assembly 3 are the same, or to avoid that the oil storage assembly 4 is drove to fall out when users want to remove the battery component 2.

Figure 10:
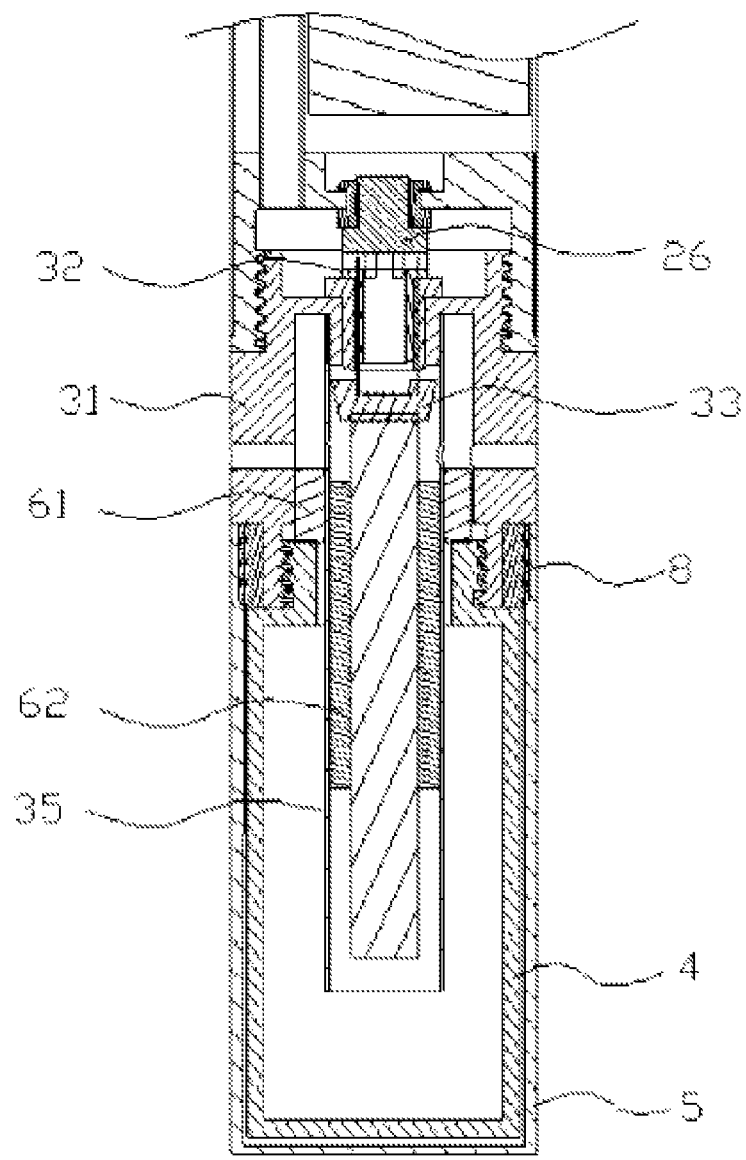
FIG. 10 is a cutaway view of the electronic cigarette provided by a second embodiment of the present application.

The first embodiment shows a connecting method of the protective sleeve 5 and the atomization assembly 3, and the second embodiment provides other connecting methods, refer to FIG. 10, the only one difference between the second embodiment and the first embodiment is that the protective sleeve 5 in the second embodiment is interference fitted with the atomization assembly 3, a compression ring 8 is arranged at a connection point of the atomization assembly 3 and the oil storage assembly 4, Therefore, a position of the first connecting piece 31 in the first embodiment which is provided with the first external thread is amended to sleeve the compression ring 8, other components and connecting methods are the same with the first embodiment, and do not be described in details here. The protective sleeve 5 is sheathed on the compressing ring 8, the protective sleeve 5 is removed firstly when filling in or replacing the cigarette oil. Wherein, the compression ring 8 is an elastic product.

As an interference fit is a kind of non-contacting connection methods, it can greatly reduce the transmission of vibration, strengthen the anti-shock performance of an end of the oil storage assembly of the electronic cigarette, and overcome the defects of the prior art in fragile oil bottle.

Two connection modes of the protective sleeve 5 and the atomization assembly 3 is provided, but a specific defining method is not limited to the implementation of this example, it can be any other detachable connection modes, for example, inserting and buckling connection etc.

In general, in the present invention, by defining the oil storage assembly on an opposite aside of the smoking end, the smoke passage does not pass through the oil storage assembly, users can be effectively prevented from sucking the non-atomized cigarette oil; and meanwhile, through the arrangement of a protective sleeve for containing the tar storage device on the electronic cigarette, the vibration-resistance of the tar storage device can be enhanced, so that the risk that the tar storage bottle is easily broken is avoided.

Above illustrated embodiments of the present invention with attached figures, which are only some preferable embodiments of the present invention, cannot be utilized to limit the claim scope of the present invention. The specific implementation of the above is only schematic, rather than restrictive. It should be understood that, in the inspiration of the present application, those skilled in the art who appreciate and realize all or part of the process in above embodiments may make many modifications or alternatives, without going beyond the purpose and the scope the claims intend to protect of the present application. All these belong to the protection of the present application.

What is claimed is:

1. An electronic cigarette with oil observation strip comprising an electronic cigarette body,
    wherein the electronic cigarette body is provided with a smoking end (1), an oil storage assembly (4) for containing cigarette oil, an atomization assembly (3) for atomizing the cigarette oil and a battery component (2) for powering the atomization assembly (3); the oil storage assembly (4) is arranged on one end of the electronic cigarette body which is on an opposite side of the smoking end (1),
    wherein the electronic cigarette further comprises a protective sleeve (5) for containing the oil storage assembly (4); and
    an observation zone which is used for observing an amount of the cigarette oil in the oil storage assembly (4) is defined on the protective sleeve (5);
    wherein the observation zone is a strip through hole (51) or a strip transparent piece which is defined along an axial direction of the electronic cigarette; and
    wherein a bottom of the protective sleeve (5) which is on an opposite side of the smoking end (1) is a cambered surface, or an arc protrusion (53) is formed along an axial direction of the protective sleeve (5) and extends toward an opposite side of the smoking end (1), the cambered surface or the arc protrusion (53) is provided with a pattern (9).

2. The electronic cigarette according to claim 1, wherein the oil storage assembly (4) is a transparent glass product or a ceramic product, and the protective sleeve (5) is a metal product, a wood product or a foam product.

3. The electronic cigarette according to claim 1, wherein the oil storage assembly (4) is detachably connected with the atomization assembly (3);
    and/or
    the atomization assembly (3) is detachably connected with the battery component (2).

4. The electronic cigarette according to claim 1, wherein the atomization assembly (3) is coaxially defined with the battery component (2).

5. The electronic cigarette according to claim 1, wherein the atomization assembly (3) is connected with the oil storage assembly (4) by a thread connection, the atomization assembly (3) is connected with the battery component (2) by an inserting connection.

6. The electronic cigarette according to claim 1, wherein a first sealing ring (61), which is used for sealing the oil storage assembly (4), is defined at a detachable connection point of the atomization assembly (3) and the oil storage assembly (4);
   or, a ring sealing plug configuring with a through hole is defined at a mouth of the oil storage assembly (4) to seal the oil storage assembly (4), a film which is used to seal the oil storage assembly (4) is defined inside the through hole of the ring sealing plug, and the film can be pierced.

7. The electronic cigarette according to claim 1, wherein the atomization assembly (3) comprises:
   a heating coil assembly (33) which is used for atomizing the cigarette oil;
   an oil guide device which is used to transfer the cigarette oil to the heating coil assembly (33).

8. The electronic cigarette according to claim 7, wherein the atomization assembly (3) further comprises a first connecting piece (31) which is detachably connected with the battery component (2) and the oil storage assembly (4), the first connecting piece (31) has an atomizing chamber, the heating coil assembly (33) and the oil guide device are installed inside the atomizing chamber, the oil guide device comprises an oil guide cotton (34) and an atomization sleeve (35) which is sheathed on the oil guide cotton (34), one end of the oil guide cotton (34) and the atomization sleeve (35) extend inside the oil storage assembly (4), at least one oil transferring hole is defined on an area of a peripheral wall of the atomization sleeve (35) which is arranged inside the oil storage assembly (4), the cigarette oil is transferred to the oil guide cotton (34) by the oil transferring hole and then the cigarette oil is transferred to the heating coil assembly (33) to be atomized.

9. The electronic cigarette according to claim 1, wherein, the battery component (2) comprises a battery sleeve (21), a battery (22) which is defined along an axial direction of the battery sleeve (21), and an airflow control module (28), the smoking end (1) is a suction nozzle which is connected to an end of the battery sleeve (21) which is on an opposite side of the oil storage assembly (4), the suction nozzle is provided with an air inlet (11) which is communicated with an inside part of the battery sleeve (21).

10. The electronic cigarette according to claim 9, wherein the battery component (2) further comprises a vent tube (27) which is defined along an axial direction of the battery component (2), the vent tube (27) is used to communicated the air inlet (11) with a part of a smoke passage of the atomization assembly (3).

11. The electronic cigarette according to claim 1, wherein the atomization assembly (3) is located between the battery component (2) and the oil storage assembly (4), and the smoking end (1) is defined outside an end of the battery component (2), or the smoking end (1) is placed in a middle part of the battery component (2), or the smoking end (1) is arranged at a position of the battery component (2) which is an opposite side of the atomization assembly (3).

12. The electronic cigarette according to claim 11, wherein the protective sleeve (5) is detachably connected with the atomization assembly (3).

13. The electronic cigarette according to claim 12, wherein the protective sleeve (5) is connected with the atomization assembly (3) by a thread connection, the protective sleeve (5) has a first internal thread (52), the atomization assembly (3) comprises a first connecting piece (31), the first connecting piece (31) has a first external thread which is matched with the first internal thread (52).

14. The electronic cigarette according to claim 12, wherein the protective sleeve (5) is interference fitted with the atomization assembly (3), a compression ring (8) is arranged at a connection point of the atomization assembly (3) and the oil storage assembly (4), the protective sleeve (5) is sheathed on the compressing ring (8).

\* \* \* \* \*